United States Patent
Schönfeld et al.

(10) Patent No.: US 10,556,969 B2
(45) Date of Patent: *Feb. 11, 2020

(54) CHIMERIC ANTIGEN RECEPTORS WITH AN OPTIMIZED HINGE REGION

(71) Applicant: CHEMOTHERAPEUTISCHES FORSCHUNGSINSTITUT GEORG-SPEYER-HAUS, Frankfurt am Main (DE)

(72) Inventors: Kurt Schönfeld, Langen (DE); Christiane Schönfeld, Langen (DE); Winfried Wels, Frankfurt am Main (DE)

(73) Assignee: CHEMOTHERAPETICSHES FORSHUNGSINSTITUT GEORG-SPEYER-HAUS, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/726,943

(22) Filed: Oct. 6, 2017

(65) Prior Publication Data

US 2018/0022828 A1 Jan. 25, 2018

Related U.S. Application Data

(60) Continuation of application No. 14/928,794, filed on Oct. 30, 2015, now Pat. No. 9,815,908, which is a division of application No. 13/821,491, filed as application No. PCT/EP2011/004490 on Sep. 6, 2011, now Pat. No. 9,212,229.

(30) Foreign Application Priority Data

Sep. 8, 2010 (EP) .................................. 10009345

(51) Int. Cl.
| | | |
|---|---|---|
| C07K 16/46 | (2006.01) | |
| C07K 16/32 | (2006.01) | |
| C12N 15/70 | (2006.01) | |
| C12N 15/62 | (2006.01) | |
| C12N 15/63 | (2006.01) | |
| C07K 14/725 | (2006.01) | |
| C07K 14/705 | (2006.01) | |

(52) U.S. Cl.
CPC .......... *C07K 16/46* (2013.01); *C07K 14/7051* (2013.01); *C07K 14/70517* (2013.01); *C07K 14/70521* (2013.01); *C07K 16/32* (2013.01); *C07K 2317/55* (2013.01); *C07K 2317/56* (2013.01); *C07K 2317/622* (2013.01); *C07K 2317/626* (2013.01); *C07K 2319/00* (2013.01)

(58) Field of Classification Search
CPC .. C07K 16/46; C07K 16/32; C07K 14/70521; C07K 14/70517; C07K 14/7051; C07K 2317/56; C07K 2317/55; C07K 2319/00; C07K 2317/622; C12N 15/70; C12N 15/62; C12N 15/63; C12N 5/0646
See application file for complete search history.

(56) References Cited

U.S. PATENT DOCUMENTS

| | | |
|---|---|---|
| 2004/0043401 A1 | 3/2004 | Sadelain et al. |
| 2007/0031438 A1 | 2/2007 | Junghans |
| 2008/0260738 A1 | 10/2008 | Moore et al. |

FOREIGN PATENT DOCUMENTS

| | | |
|---|---|---|
| WO | 9530014 | 11/1995 |
| WO | 2008045437 A2 | 4/2008 |

OTHER PUBLICATIONS

Rudikoff et al., Proc Natl Acad Sci USA 79: 1979-1983 (Year: 1982).*
Wu et al., J. Mol. Biol. 294: 151-162 (Year: 1999).*
Lloyd et al., Protein Engineering, Design & Selection 22:159-168 (Year: 2009).*
Edwards et al., J Mol Biol. 334(1): 103-118 (Year: 2003).*
Boursier, Jean Philippe et al., "Evidence for an Extended Structure of the T-cell Co-receptor CD8α as Deduced from the Hydrodynamic Properties of Soluble Forms of the Extracellular Region," The Journal of Biological Chemistry, 1993, 268(3):2013-2020.
Classon, Brendan J. et al., "The hinge region of the CD8α chain: structure, antigenicity, and utility in expression of immunoglobulin superfamily domains," International Immunology, Feb. 1992, 4(2):215-225.
Dall, Peter et al., "In vivo cervical cancer growth inhibition by genetically engineered cytotoxic T cells." Cancer Immunol. Immunother., Jan. 2005, 54: Abstract.
Fitzer-Attas, Cheryl J. et al., "Harnessing Syk Family Tyrosine Kinases as Signaling Domains for Chimeric Single Chain of the Variable Domain Receptors: Optimal Design for T Cell Activation," Journal of Immunology, Jan. 1998, 160(1):145-154.
Moore, L.J. et al., "Characterisation of salmon and trout CD8α and CD8β," Molecular Immunology, 2005, 42:1225-1234.
Nolan, K.F. et al., "Bypassing Immunization: Optimized Design of "Designer T Cells" against Carcinoembryonic Antigen (CEA)-expressing Tumors, and Lack of Suppression by Soluble CEA," Clinical Cancer Research, Dec. 1999, 5(12):3928-3941.

(Continued)

*Primary Examiner* — Phuong Huynh
(74) *Attorney, Agent, or Firm* — Saliwanchik, Lloyd & Eisenschenk

(57) ABSTRACT

The present invention relates to multi-functional proteins which comprise (i) a signal peptide, (ii) a target specific recognition domain, (iii) a linker region, connecting domain (ii) and domain (iv) which comprises a specific modified hinge region of the human CD8 alpha-chain, and (iv) an effector domain. The present invention furthermore relates to nucleic acids encoding the proteins, expression constructs for expressing the protein in a host cell and host cells. The proteins of the invention are chimeric antigen receptors with an optimized linker or hinge region that are suitable for generating target-specific effector cells, for use as a medicament, in particular in the treatment of cancer and in adoptive, target-cell specific immunotherapy.

8 Claims, 5 Drawing Sheets

Specification includes a Sequence Listing.

(56) References Cited

OTHER PUBLICATIONS

Rohrbach, Florian et al., "Targeted Delivery of the ErbB2/HER2 Tumor Antigen to Professional APCs Results in Effective Antitumor Immunity," Journal of Immunology, May 2005, 174(9):5481-5489.
Sadelain, Michel et al., "The promise and potential pitfalls of chimeric antigen receptors," Current Opinion in Immunology, 2009, 21: 215-223.

* cited by examiner

Amino acid sequence of hinge region derived from CD8 alpha-chain

ALSNSIMYFSHFVPVFLPAKPTTTPAPRPPTPAPTIASQPLSLRPEACRPAAGGAVHTRGLD
(SEQ ID NO:1)

Amino acid sequence of modified hinge derived from CD8 alpha-chain

ALSNSIMYFSHFVPVFLPAKPTTTPAPRPPTPAPTIASQPLSLRPEASRPAAGGAVHTRGLD
(SEQ ID NO:2)

CHIMERIC ANTIGEN RECEPTORS WITH AN OPTIMIZED HINGE REGION

CROSS REFERENCE TO RELATED APPLICATIONS

This application is a continuation application of application Ser. No. 14/928,794, filed Oct. 30, 2015; which is a divisional application of application Ser. No. 13/821,491, filed May 28, 2013, now U.S. Pat. No. 9,212,229; which is a National Stage Application of International Application Number PCT/EP2011/004490, filed Sep. 6, 2011; which claims priority to European Patent Application No. 10009345.9, filed Sep. 8, 2010; all of which are incorporated herein by reference in their entirety.

The Sequence Listing for this application is labeled "SeqList-14May13-ST25.txt", which was created on May 14, 2013, and is 25 KB. The entire content is incorporated herein by reference in its entirety.

The present invention relates to multi-functional proteins which comprise (i) a signal peptide, (ii) a target specific recognition domain, (iii) a linker region, connecting domain (ii) and domain (iv) which comprises a specific modified hinge region of the human CD8 alpha-chain, and (iv) an effector domain. The present invention furthermore relates to nucleic acids encoding the proteins, expression constructs for expressing the protein in a host cell and host cells. The proteins of the invention are chimeric antigen receptors with an optimized linker or hinge region that are suitable for generating target-specific effector cells, for use as a medicament, in particular in the treatment of cancer and in adoptive, target-cell specific immunotherapy.

BACKGROUND OF THE INVENTION

T lymphocytes recognize specific antigens through interaction of the T cell receptor (TCR) with short peptides presented by major histocompatibility complex (MHC) class I or II molecules. For initial activation and clonal expansion, naïve T cells are dependent on professional antigen-presenting cells (APCs) that provide additional co-stimulatory signals. TCR activation in the absence of co-stimulation can result in unresponsiveness and clonal anergy. To bypass immunization, different approaches for the derivation of cytotoxic effector cells with grafted recognition specificity have been developed. Chimeric antigen receptors (CARs) have been constructed that consist of binding domains derived from natural ligands or antibodies specific for cell-surface antigens, genetically fused to effector molecules such as the TCR alpha and beta chains, or components of the TCR-associated CD3 complex. Upon antigen binding, such chimeric antigen receptors link to endogenous signaling pathways in the effector cell and generate activating signals similar to those initiated by the TCR complex. Since the first reports on chimeric antigen receptors, this concept has steadily been refined and the molecular design of chimeric receptors has been optimized (for a review see Uherek et al., 2001). Aided by advances in recombinant antibody technology, chimeric antigen receptors targeted to a wide variety of antigens on the surface of cancer cells and of cells infected by human immunodeficiency virus (HIV) have been generated (for a review see Uherek et al., 2001).

US 2007/0031438 A1 describes a CAR comprising a binding domain of an antibody against prostate specific membrane antigen (PSMA), a modified CD8 hinge in which at least one of the cysteine residues has been mutated and a zeta signaling domain of the T cell receptor. In particular, US 2007/0031438 A1 uses a human CD8 hinge region with amino acid positions 135 to 180 (according to the amino acid numbering of Swissprot P01732), wherein the cysteine in position 164 is substituted with alanine.

Fitzer-Attas et al. (1998) describe a CAR comprising a non modified CD8 hinge region with amino acid positions 116 to 208 (according to the amino acid numbering of Swissprot P01732), which comprises three cysteine residues at positions 164, 181 and 206. The chimeric receptor furthermore uses kinase domains as effector domain.

WO 2008/045437 A2 describes CARs comprising as an extracellular binding portion, a single chain antibody portion that binds to EGFRvIII, a transmembrane portion derived from human CD8 alpha or CD28, and an intracellular signaling portion derived from human CD3 zeta. In particular, WO 2008/045437 A2 describes chimeric T cell receptor proteins with a non modified CD8 hinge region with amino acid positions 135 to 205, 135 to 203 or 135 to 182 (according to the amino acid numbering of Swissprot P01732), each comprising cysteine residues in positions 164 and 181.

WO 95/30014 A1 describes a CAR comprising an antigen binding domain derivable from a monoclonal antibody directed against a suitable antigen on a tumor cell (such as scFv(FRPS)), a hinge region comprising from 40 to 200 amino acids and a functional zeta chain derivable from the T cell antigen receptor. In particular, the CAR of WO 95/30014 A1 uses the non modified murine CD8 hinge region with amino acid positions 132 to 191 (according to the amino acid numbering of Swissprot P01731), comprising a cysteine residue in position 178.

US 2008/0260738 A1 describes antibody fusion proteins comprising at least two Fc monomers and at least one linker, wherein a modified CD8 hinge region is used for linking the two Fc monomers. In particular, US 2008/0260738 A1 uses modified CD8 hinge regions with amino acid positions 131 to 170 or 136 to 169 (according to the amino acid numbering of Swissprot P01732), wherein the cysteine in position 164 is substituted with serine.

The present invention aims to provide optimized chimeric antigen receptors which allow more efficient surface expression and high functionality in lymphocytes.

It is a further objective of the present invention to provide means and methods for generating antigen-specific effector cells as well as means and methods for the use in adoptive, target-cell specific immunotherapy and for treatment of cancer.

SUMMARY OF THE INVENTION

According to the present invention this object is solved by a multi-functional or multi-domain protein comprising
 (i) a signal peptide;
 (ii) a target specific recognition domain;
 (iii) a linker region, connecting domain (ii) and domain (iv); and
 (iv) an effector domain.

According to the invention, the linker region (iii) is a modified hinge region of the human CD8 alpha-chain, wherein the human CD8 alpha-chain hinge region is modified by replacing the cysteine residue(s) with (a) serine residue(s) or deleting the cysteine residue(s); and wherein the amino acid sequence of the modified hinge region of the human CD8 alpha-chain has at least 95% sequence identity to the amino acid sequence of SEQ ID NO: 2 or wherein the linker region (iii) has the amino acid sequence of SEQ ID NO: 2.

According to the present invention this object is furthermore solved by a nucleic acid encoding the multi-functional protein.

According to the present invention this object is furthermore solved by an expression construct for expressing the multi-functional protein.

According to the present invention this object is furthermore solved by a host cell expressing the multi-functional protein or comprising the nucleic acid or the expression construct.

According to the present invention this object is furthermore solved by using the multi-functional protein, nucleic acid, or expression construct for generating antigen-specific effector cells.

According to the present invention this object is furthermore solved by the multi-functional protein, nucleic acid, expression construct or host cell for use as a medicament.

According to the present invention this object is furthermore solved by the multi-functional protein, nucleic acid, expression construct or host cell for use in the treatment of cancer.

According to the present invention this object is furthermore solved by the multi-functional protein, nucleic acid, expression construct or host cell for use in adoptive, target-cell specific immunotherapy.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Multi-functional, Multi-domain Proteins

As described above, the present invention provides multi-functional proteins comprising several domains, namely (i) a signal peptide;
(ii) a target specific recognition domain;
(iii) a linker region, connecting domain (ii) and domain (iv); and
(iv) an effector domain.

The multi-functional proteins of the invention are chimeric antigen receptors characterized by an optimized hinge region (linker region).

The proteins of the invention are preferably cell surface receptor proteins and, thus, comprise an extracellular portion (domains (i) and (ii) and (iii)), a transmembrane portion (contributed by/comprised in domain (iv)) and a cytoplasmic portion (contributed by/comprised in domain (iv)), and can thus be inserted into the plasma membrane of the host cell. The functionality of the proteins of the invention within a host cell is detectable in an assay suitable for demonstrating the signaling potential of said protein upon binding of a particular ligand. Such assays are available to the skilled artisan.

Upon binding to the target, such chimeric antigen receptors link to endogenous signaling pathways in a cell (an effector cell) and generate certain activating signals (depending on the effector domain).

The expression of chimeric antigen receptors (CAR) with defined target specificity (such as target-cell specificity) in lymphocytes and other effector cells of the immune system (such as T cells or natural killer (NK) cells) results in genetically modified variants of said cells that selectively target and eliminate defined targets, including but not limited to malignant cells carrying a respective tumor-associated surface antigen or virus infected cells carrying a virus-specific surface antigen or target cells carrying a lineage-specific or tissue-specific surface antigen. Thus, said expression of CARs generates antigen-specific effector cells for the use in adoptive, target-cell specific immunotherapy. CARs are composed of a target specific recognition domain or cell recognition domain (domain (ii), such as a scFv antibody fragment) for recognition of a target (such as a tumor-cell surface antigen) fused via a flexible linker region to an effector domain (comprising a transmembrane region and one or more intracellular signaling domains like the zeta-chain of the CD3 complex of the T-cell receptor). CAR expression retargets the cytotoxic activity of the effector cells (lymphocytes) to targets (tumor cells) and triggers their cytolysis by the CAR expressing immune effector cells. Thereby binding of the target specific recognition domain of the CAR to its cognate target on the surface of target cells/viruses transmits a signal into the CAR expressing immune effector cells via the intracellular signaling domain(s) of the CAR which activates the endogenous cytotoxic activity of such immune effector cells.

(i) The Signal Peptide

A "signal peptide" refers to a peptide sequence that directs the transport and localization of the protein within a cell, e.g. to a certain cell organelle (such as the endoplasmic reticulum) and/or the cell surface.

The signal peptide (i) is a signal peptide of any secreted or transmembrane human protein of type 1 (extracellular N-terminus), which allows the transport of the multi-functional protein of the invention to the cell membrane and cell surface and allows correct localization of the multi-functional protein of the invention, in particular the extracellular portion (domains (i) and (ii) and (iii)) on the cell surface; the transmembrane portion (contributed by/comprised in domain (iv)) inserted into the plasma membrane and the cytoplasmic portion (contributed by/comprised in domain (iv)) in the host cell.

Preferably, the signal peptide is cleaved after passage of the endoplasmic reticulum (ER), i.e. is a cleavable signal peptide.

In an embodiment, the signal peptide (i) comprises or is immunoglobulin heavy chain signal peptide.

(ii) The Target Specific Recognition Domain

The target specific recognition domain (ii) binds an antigen, receptor, peptide ligand or protein ligand of the target.

The target specific recognition domain (ii) preferably comprises an antigen binding domain derived from an antibody against an antigen of the target, or a peptide binding an antigen of the target, or a peptide or protein binding an antibody that binds an antigen of the target, or a peptide or protein ligand (including but not limited to a growth factor, a cytokine or a hormone) binding a receptor on the target, or a domain derived from a receptor (including but not limited to a growth factor receptor, a cytokine receptor or a hormone receptor) binding a peptide or protein ligand on the target.

Preferably, the target is a cell or a virus.

The target specific recognition domain serves for the targeting of the multi-functional protein or a respective cell expressing/carrying the multi-functional protein on its surface to a specific target. Binding of the target specific recognition domain of the multi-functional protein (CAR) to its cognate target on the surface of target cells/viruses furthermore transmits a signal into the multi-functional protein (CAR)-expressing immune effector cells via the intracellular signaling domain(s) of the multi-functional protein which activates the endogenous cytotoxic activity of such imune effector cells.

Preferably, the antigen of the target is a tumor-associated surface antigen
  including but not limited to ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, a major histocompatibility complex (MHC) molecule presenting a tumor-specific peptide epitope,
or
a lineage-specific or tissue-specific tissue antigen
  including but not limited to CD3, CD4, CD8, CD24, CD25, CD33, CD34, CD133, CD138, CTLA-4, B7-1 (CD80), B7-2 (CD86), endoglin, a major histocompatibility complex (MHC) molecule,
or
a virus-specific surface antigen,
  including but not limited to an HIV-specific antigen (such as HIV gp120), an EBV-specific antigen, a CMV-specific antigen, a HPV-specific antigen, a HBV-specific antigen, a HCV-specific antigen, a Lassa Virus-specific antigen, an Influenza Virus-specific antigen.

In an embodiment, where domain (ii) is derived from an antigen binding domain, the antigen binding domain is preferably derived from an antibody or an antibody fragment, such as a single chain Fv (scFv) fragment, a Fab fragment, a diabody, a variable domain of the antibody heavy chain or antibody light chain.

In an embodiment of the invention, the antigen of the target is the tumor-associated surface antigen ErbB2 and the antigen binding domain of domain (ii) is from an ErbB2-specific scFv.

(iii) The Linker Region

The linker region (iii) connects the target specific recognition domain (ii) and the effector domain (iv).

The linker region serves as a flexible spacer between the target specific recognition domain (ii) and the effector domain (iv). It ensures the necessary accessibility and flexibility of the target specific recognition domain (ii). The linker region is understood to be essential for the functionality of the multi-functional proteins of the invention.

Current CAR constructs contain a linker region derived from the alpha-chain of the murine or human CD8 molecule which provides a flexible connection between cell-targeting and signaling/effector domains (Uherek et al., 2002; Muller et al., 2008). However, unpaired cysteine(s) present in the linker region of the CD8 alpha-chain can result in unwanted covalent intra- or intermolecular bonds of CAR molecules which negatively affects surface expression of CAR as well as CAR functionality.

Object matter of the invention is the generation of optimized CAR constructs which do not faun such non-productive covalent linkages via the unpaired cysteine residue of the human CD8 alpha-chain and facilitate efficient surface expression and high functionality in lymphocytes.

This is achieved, according to the invention, by employing a specific fragment of the hinge region derived from the human CD8 alpha-chain ranging from amino acid positions 117 to 178 (numbering according to the sequence of human T-cell surface glycoprotein CD8 alpha chain; Swiss-Prot accession number P01732), and by modifying the amino acid sequence of the hinge region derived from the human CD8 alpha-chain, in particular by replacing/converting the unpaired cysteine(s) to (a) serine residues or by deleting the unpaired cysteine(s). The resulting optimized CAR construct is expressed at higher levels at the cell surface and mediates more potent antigen-specific killing. In comparison to cells carrying a current CAR, cells carrying the optimized CAR construct contain a lower level of unpaired endogenous effector domain (such as CD3 zeta-chain) but higher levels of functional receptor complexes and productive dimers between CAR and endogenous effector domain (such as CD3 zeta-chain).

In particular, the linker region (iii) comprises a modified hinge region of the human CD8 alpha-chain.

The sequence of human T-cell surface glycoprotein CD8 alpha chain (Swiss-Prot accession number P01732 (CD8A_HUMAN)) [SEQ ID NO: 13]

```
         10          20          30          40
MALPVTALLL  PLALLLHAAR  PSQFRVSPLD  RTWNLGETVE 50          60          70          80
LKCQVLLSNP  TSGCSWLFQP  RGAAASPTFL  LYLSQNKPKA 90         100         110         120
AEGLDTQRFS  GKRLGDTFVL  TLSDFRRENE  GYYFCSALSN 130         140         150         160
SIMYFSHFVP  VFLPAKPTTT  PAPRPPTPAP  TIASQPLSLR 170         180         190         200
PEACRPAAGG  AVHTRGLDFA  CDTYIWAPLA  GTCGVLLLSL 210         220         230
VITLYCNHRN  RRRVCKCPRP  VVKSGDKPSL  SARYV
``` wherein the flexible hinge region are amino acid residues 117 to 178 [SEQ ID NO: 1]:

ALSNSIMYFSHFVPVFLPAKPTTTPAPRPPTPAPTIASQPLSLRPEA<u>C</u>RP

AAGGAVHTRGLD

The modification of the human CD8 alpha-chain hinge region according to the invention is the replacement of the cysteine residue(s) with (a) serine residue(s) or the deletion of the cysteine residue(s).

According to the invention, the linker region (iii) consists of the amino acid sequence of SEQ ID NO: 2:

ALSNSIMYFSHFVPVFLPAKPTTTPAPRPPTPAPTIASQPLSLRPEA<u>S</u>RP

AAGGAVHTRGLD or an amino acid sequence that has at least 95% sequence identity or 99% sequence identity to the amino acid sequence of SEQ ID NO: 2, under the proviso that amino acid residue no. 48 of SEQ ID NO: 2 is not a cysteine and is a serine and under the proviso that the amino acid sequence does not contain any cysteine residue(s), or an amino acid sequence that differs in one, two or three amino acid residues from the amino acid sequence of SEQ ID NO: 2, under the proviso that amino acid residue no. 48 of SEQ ID NO: 2 is not a cysteine and is a serine and under the proviso that the amino acid sequence does not contain any cysteine residue(s), wherein "differ" refers to replacement/substitution, addition or deletion, such as conservative substitution(s) of amino acid residues.

Thus, the linker region (iii) does not contain any cysteine residue(s).

Thus, the linker region (iii) is selected from any of the following:
the amino acid sequence of SEQ ID NO: 2,
an amino acid sequence with at least 95% sequence identity to SEQ ID NO: 2 under the proviso that amino acid residue 48 is not a cysteine and is a serine,
and
an amino acid sequence that differs in one, two or three amino acid residues from the amino acid sequence of SEQ ID NO: 2 under the proviso that amino acid residue 48 is not a cysteine and is a serine.

As discussed above, prior art describes chimeric antigen receptors that contain as linker regions different fragments of the hinge region derived from the human or murine CD8 alpha-chain. However, the specific modified hinge region of the invention that is used as the linker region (iii) in the multi-functional proteins according to the invention has not been used or disclosed in the art and has been found by the inventors to be particularly advantageous for the expression of the multi-functional proteins/CARs according to the invention and their transport to the surface of the effector cells (as has been demonstrated in this specification e.g. in FIGS. 3A-3B and 4). Furthermore, the specific modified hinge region of the invention results in improved functionality of the multi-functional proteins/CARs according to the invention (as has been demonstrated in this specification e.g. in FIGS. 4 and 5C). This improved expression and functionality of CARs according to the invention is due to the selection and specific modification of amino acid residues 117 to 178 from the human CD8 alpha-chain as the linker region (iii) in the multi-functional proteins. The specific modified hinge region of the invention that is used as the linker region (iii) in the multi-functional proteins according to the invention prevents the occurence of unpaired cysteines by not including the cysteines naturally present at amino acid positions 115 and 181 of the human CD8 alpha-chain, and replacement of the cysteine residue naturally present at amino acid position 164 of the human CD8 alpha-chain with a chemically similar serine residue. Furthermore, the length of 62 amino acid residues of the specific modified hinge region of the invention that is used as the linker region (iii) in the multi-functional proteins according to the invention ensures optimal spatial distance of the N-terminally attached target specific recognition domain (ii) from the C-terminally attached transmembrane and intracellular effector domain (iv), providing high flexibility and efficiency of target cell recognition. In contrast, prior art describes CARs employing as linker regions unmodified fragments of the hinge region from the human CD8 alpha-chain (see, for example, Fitzer-Attas et al. 1998, WO 2008/045437) or murine CD8 alpha-chain (see, for example, WO 95/30014) that contain naturally occurring cysteines of the CD8 alpha-chain, which can negatively affect expression and functionality of these CARs through the formation of undesired intra- or intermolecular disulfide bonds. Furthermore, prior art describes CARs employing as linker regions modified fragments of the hinge region from the human CD8 alpha-chain that encompass significantly shorter amino acid sequences (such as only about 30 to about 40 amino acid residues, see, for example, US 2007/0031438), which reduces spatial distance of the target specific recognition domain from the effector domain and can negatively affect flexibility and efficiency of target cell recognition.

(iv) The Effector Domain

The effector domain (iv) comprises a transmembrane region and one or more intracellular signaling domains.

The effector domain serves the coupling of the target/antigen recognition to the intracellular signaling machinery.

Binding of the target specific recognition domain (ii) of the multi-functional protein (CAR) to its cognate target on the surface of target cells/viruses furthermore transmits a signal into the multi-functional protein (CAR)-expressing immune effector cells via the intracellular signalling domain(s) of the multi-functional protein (which are part of the effector domain) which activates the endogenous cytotoxic activity of such immune effector cells.

Preferably, the effector domain (iv) comprises or consists of (is)
(a) the zeta-chain of the human CD3 complex of the T-cell receptor or fragment(s) thereof; or a functional equivalent thereof,
(b) a fusion of a fragment of the human costimulatory CD28 receptor fused to a fragment of the zeta-chain of the human CD3 complex of the T-cell receptor, preferably a fusion of the transmembrane and intracellular domain of human CD28 with the intracellular domain of human CD3 zeta chain; or a functional equivalent thereof.

The term "functional equivalent" defines a protein or nucleotide sequence, having a different amino acid or base sequence, compared to the sequences disclosed herein, but exhibiting the same function in vitro and in vivo. An example of a functional equivalent is a modified or synthetic gene, encoding the expression of a protein identical or highly homologous to that encoded by the wildtype gene or a sequence disclosed herein.

(a) The sequence of human T-cell surface glycoprotein CD3 zeta chain (Swiss-Prot accession number P20963 (CD3Z_HUMAN); Isoform 3) [SEQ ID NO: 3]

```
         10           20          30           40
MKWKALTTAA  TLQAQLPITE  AQSFGLLDPK  LCYLLDGILF 50           60          70           80
TYGVILTALF  LRVKFSRSAD  APAYQQGQNQ  LYNELNLGRR 90          100         110          120
EEYDVLDKRR  GRDPEMGGKP  RRKNPQEGLY  NELQKDKMAE 130          140         150          160
AYSEIGMKGE  RRRGKGHDGL  YQGLSTATKD  TYDALHMQAL  PPR
```

The effector domain (iv) comprises or consists of (is) an amino acid sequence with SEQ ID NO: 3 or fragment(s) thereof (preferably the transmembrane and intracellular domain of human CD3 zeta-chain, more preferably amino acid residues 29 to 163 of amino acid sequence with SEQ ID NO: 3) or a functional equivalent thereof, wherein a "functional equivalent" has less sequence identity (such as at least 80% sequence identity, preferably at least 90% sequence identity, more preferably at least 95% sequence identity or 99% sequence identity) but is a functional zeta-chain of the CD3 complex of the T-cell receptor.

According to the invention, the zeta chain is of human origin. Within the TCR the CD3 zeta chain exists as a disulfide homodimer. A "functional CD3 zeta chain" or "a functional zeta-chain of the CD3 complex of the T-cell receptor" is a protein which upon expression in T cell hybridomas deficient in endogenous zeta expression is capable of restoring in said hybridomas a functionally active TCR.

(b) The fusion of a fragment of the costimulatory CD28 receptor fused to a fragment of the zeta-chain of the CD3 complex of the T-cell receptor contains:
(b1) the transmembrane domain of human CD28;
(b2) the intracellular domain of human CD28;
(b3) the intracellular domain of human CD3 zeta chain;

The sequence of human T-cell-specific surface glycoprotein CD28 (Swiss-Prot accession number P10747 (CD28_HUMAN)) [SEQ ID NO: 4]

```
            10         20         30         40
    MLRLLLALNL FPSIQVTGNK ILVKQSPMLV AYDNAVNLSC 50         60         70         80
    KYSYNLFSRE FRASLHKGLD SAVEVCVVYG NYSQQLQVYS 90        100        110        120
    KTGFNCDGKL GNESVTFYLQ NLYVNQTDIY FCKIEVMYPP 130        140        150        160
    PYLDNEKSNG TIIHVKGKHL CPSPLFPGPS KPFWVLVVVG 170        180        190        200
    GVLACYSLLV TVAFIIFWVR SKRSRLLHSD YMNMTPRRPG 210        220
    PTRKHYQPYA PPRDFAAYRS
``` wherein (b 1) are preferably amino acid residues 151-180 of SEQ ID NO: 4, (b2) are amino acid residues 181-220 of SEQ ID NO: 4 and (b3) are amino acid residues 52-163 of SEQ ID NO: 3 (=SEQ ID NO: 5):

```
    KPFWVLVVVG GVLACYSLLV TVAFIIFWVR SKRSRLLHSD

YMNMTPRRPG PTRKHYQPYA PPRDFAAYRS RVKFSRSADA

PAYQQGQNQL YNELNLGRRE EYDVLDKRRG RDPEMGGKPR

RKNPQEGLYN ELQKDKMAEA YSEIGMKGER RRGKGHDGLY

QGLSTATKDT YDALHMQALP PR
```

The effector domain (iv) comprises or consists of (is) an amino acid sequence with the amino acid sequence of SEQ ID NO: 5 or a functional equivalent thereof, wherein a "functional equivalent" has less sequence identity (such as at least 80% sequence identity, preferably at least 90% sequence identity, more preferably at least 95% sequence identity or 99% sequence identity) but is a functional fusion of the costimulatory CD28 receptor fused to a fragment of the zeta-chain of the CD3 complex of the T-cell receptor.

Preferably, the multi-functional protein according to the invention comprises or consists of the amino acid sequence of a (cleavable) signal peptide (i), an scFv (ii), the modified hinge region (iii) (as defined herein, preferably of SEQ ID NO: 2) and the CD3 zeta chain or fragment(s) thereof or a fusion of fragment(s) of CD28 with fragment(s) of CD3 zeta-chain (iv) (wherein the signal peptide is at the N-terminus and the zeta chain/fusion is at the C-terminus).

In a preferred embodiment, the protein comprises or consists of the amino acid sequence of SEQ ID NO: 6; or an amino acid sequence that has at least 95% sequence identity or 99% sequence identity to the amino acid sequence of SEQ ID NO: 6 (under the proviso that amino acid residue no. 308 (i.e. amino acid residue no. 48 of the modified hinge region (SEQ ID NO: 2)) is not a cysteine and is a serine and under the proviso that the amino acid sequence of the modified hinge region (i.e. amino acid residues no. 261 to 322) does not contain any cysteine residue(s).

The amino acid sequence of SEQ ID NO: 6 refers to the amino acid sequence of the multi-functional protein with the domains:
(i) [signal peptide]—(ii)[anti-ErbB2 scFv]—(iii)[modified hinge]—(iv)[transmembrane and intracellular domain of the human CD3 zeta chain]

MDWIWRILFLVGAATGAHS*QVQLQQSGPELKKPGETVKISCKASGYPFTN*

*YGMNWVKQAPGQGLKWMGWINTSTGESTFADDFKGRFDFSLETSANTAYL*

*QINNLKSEDSATYFCARWEVYHGYVPYWGQGTTVTVSSGGGGSGGGGSGG*

*GGSDIQLTQSHKFLSTSVGDRVSITCKASQDVYNAVAWYQQKPGQSPKLL*

*IYSASSRYTGVPSRFTGSGSGPDFTFTISSVQAEDLAVYFCQQHFRTPFT*

*FGSGTKLEIK*ALSNSIMYFSHFVPVFLPAKPTTTPAPRPPTPAPTIASQP

LSLRPEASRPAAGGAVHTRGLDPKLCYLLDGILFIYGVILTALFLRVKFS

RSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALH

MQALPPR

In a preferred embodiment, the protein comprises or consists of the amino acid sequence of SEQ ID NO: 7; or an amino acid sequence that has at least 95% sequence identity or 99% sequence identity to the amino acid sequence of SEQ ID NO: 7 (under the proviso that amino acid residue no. 308 (i.e. amino acid residue no.48 of the modified hinge region (SEQ ID NO: 2)) is not a cysteine and is a serine and under the proviso that the amino acid sequence of the modified hinge region (i.e. amino acid residues no. 261 to 322) does not contain any cysteine residue(s).

The amino acid sequence of SEQ ID NO: 7 refers to the amino acid sequence of the multi-functional protein with the domains:
(i)[signal peptide]—(ii)[anti-ErbB2 scFv]—(iii)[modified hinge]—(iv)[fusion of the transmembrane and intracellular domain of human CD28 with the intracellular domain of human CD3 zeta chain].

MDWIWRILFLVGAATGAHS*QVQLQQSGPELKKPGETVKISCKASGYPFTN*

*YGMNWVKQAPGQGLKWMGWINTSTGESTFADDFKGRFDFSLETSANTAYL*

*QINNLKSEDSATYFCARWEVYHGYVPYWGQGTTVTVSSGGGGSGGGGSGG*

*GGSDIQLTQSHKFLSTSVGDRVSITCKASQDVYNAVAWYQQKPGQSPKLL*

*IYSASSRYTGVPSRFTGSGSGPDFTFTISSVQAEDLAVYFCQQHFRTPFT*

*FGSGTKLEIK*ALSNSMYFSHFVPVFLPAKPTTTPAPRPPTPAPTIASQPL

SLRPEASRPAAGGAVHTRGLDKPFWVLVVVGGVLACYSLLVTVAFIIFWV

RSKRSRLLHSDYMNMTPRRPGPTRKHYQPYAPPRDFAAYRSRVKFSRSAD

APAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQAL

PPR

Generally, a person skilled in the art is aware of the fact that some amino acid exchanges in the amino acid sequence of a protein or peptide do not have any influence on the (secondary or tertiary) structure, function and activity of the protein or peptide (at all). Amino acid sequences with such "neutral" amino acid exchanges as compared to the amino acid sequences disclosed herein fall within the scope of the present invention.

Nucleic Acids, Expression Constructs and Host Cells

As described above, the present invention provides nucleic acids/nucleic acid molecules/isolated nucleic acid molecules encoding the proteins of the invention.

The nucleic acids according to this invention comprise DNA (such as dsDNA, ssDNA, cDNA), RNA (such as dsRNA, ssRNA, mRNA), combinations thereof or derivatives (such as PNA) thereof.

Preferably, a nucleic acid of the invention comprises
  the nucleic acid encoding for the amino acid sequence of SEQ ID NO: 2; or
  the nucleic acid sequence of SEQ ID NO: 8 (=nucleotide sequence encoding for the modified hinge region)
  or their complementary sequences;
  or sequences that have at least 95% sequence identity or 99% sequence identity to the above sequences (provided that amino acid residue no. 48 of SEQ ID NO: 2 is not a cysteine and is a serine and provided that the modified hinge region does not contain any cysteine residues).

Preferably, a nucleic acid of the invention furthermore comprises
  the nucleic acid encoding for the amino acid sequence of SEQ ID NOs: 3 or 5 or for amino acid residues 29-163 of SEQ ID NO: 3; or
  the nucleic acid sequence of SEQ ID NOs: 9 or 10 (=nucleotide sequence encoding for the transmembrane and intracellular domain of human CD3 zeta chain or the fusion of the transmembrane and intracellular domain of human CD28 with the intracellular domain of human CD3 zeta chain),
  or their complementary sequences;
  or sequences that have at least 95% sequence identity or 99% sequence identity to the above sequences,
preferably fused to the nucleic acid encoding for the amino acid sequence of SEQ ID NO: 2 or the nucleic acid sequence of SEQ ID NO: 8
  or to their complementary sequences;
  or to sequences that have at least 95% sequence identity or 99% sequence identity to the above sequences SEQ ID NO: 2 or SEQ ID NO: 8 (provided that amino acid residue no. 48 of SEQ ID NO: 2 is not a cysteine and is a serine and provided that the modified hinge region does not contain any cysteine residues).

Preferably, a nucleic acid of the invention comprises or consists of
  the nucleic acid encoding for the amino acid sequence of SEQ ID NOs: 6 or 7; or
  the nucleic acid sequence of SEQ ID NOs: 11 or 12 (=nucleotide sequence encoding for the multi-functional protein with the domains (i)[signal peptide]—(ii)[anti-ErbB2 scFv]—(iii)[modified hinge]—(iv)[transmembrane and intracellular domain of the human CD3 zeta chain] or the multi-functional protein with the domains (i)[signal peptide]—(ii)[anti-ErbB2 scFv]—(iii)[modified hinge]—(iv)[fusion of the transmembrane and intracellular domain of human CD28 with the intracellular domain of human CD3 zeta chain]);
  or their complementary sequences;
  or sequences that have at least 95% sequence identity or 99% sequence identity to the above sequences (provided that amino acid residue no. 48 of SEQ ID NO: 2 is not a cysteine and is a serine and under the proviso that the amino acid sequence of the modified hinge region (i.e. amino acid residues no. 261 to 322) does not contain any cysteine residue(s)).

Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the same amino acids as the codons that are being exchanged.

Within the scope of this invention are also the nucleotide sequences obtained due to the degeneration of the genetic code of the above nucleotide sequences.

As described above, the present invention provides expression constructs for expressing the protein of the invention in a cell.

Preferably, the expression constructs further comprise promoter and terminator sequences.

An "expression or gene construct" (wherein both terms are used interchangeably throughout this specification) refers to a nucleic acid construct, usually an expression vector or plasmid, that is used to introduce a specific gene sequence into a target cell. Once the expression or gene construct is inside the cell, the protein that is encoded by the gene is produced by the cellular transcription and translation machinery. The expression or gene construct is designed to contain respective regulatory sequences that act as enhancer and promoter regions and lead to efficient transcription of the gene carried on the construct, including promoter and terminator sequences. The goal of a well-designed expression or gene construct is the production of large amounts of stable mRNA, and therefore proteins.

The skilled artisan can select further suitable components of expression or gene constructs.

The nucleic acids and/or in particular expression constructs of the invention are capable of directing the synthesis/expression of the multi-functional protein of the invention in a suitable host cell.

The nucleic acids and/or expression constructs of the invention are dsDNA, ssDNA, RNA or mRNA or combinations thereof.

As described above, the present invention provides host cells which express a protein of the invention or which comprise a nucleic acid or an expression construct of the invention.

Preferably, the host cell is selected from effector cells of the immune system, such as lymphocytes including but not limited to cytotoxic lymphocytes, T cells, cytotoxic T cells, T helper cells, Th17 T cells, natural killer (NK) cells, natural killer T (NKT) cells, mast cells, dendritic cells, killer dendritic cells, B cells.

"Effector cells" of the immune system or "immune effector cells" refers to cells of hematopoietic origin including but not limited to the cell types mentioned above that are functionally involved in the initiation and/or execution of innate and/or adaptive immune responses.

Uses of the Proteins, Nucleic Acids, Expression Constructs and Host Cells

As described above, the invention provides the use of the multi-functional protein, nucleic acid, or expression construct for generating antigen-specific effector cells.

"Antigen-specific effector cells" or "target-specific effector cells" refer to effector cells of the immune system or immune effector cells genetically modified to express the multi-functional protein of the invention by transfer of an expression construct or nucleic acid encoding said multi-functional protein. Such antigen-specific or target-specific effector cells are versatile means, in particular in the treatment of diseases (as described below for ACT and cancer treatment).

As described above, the invention provides the multi-functional protein, nucleic acid, expression construct or host cell for use as a medicament.

As described above, the invention provides the multi-functional protein, nucleic acid, expression construct or host cell for use in the treatment of cancer.

As described above, the invention provides the multi-functional protein, nucleic acid, expression construct or host cell for use in adoptive, target-cell specific immunotherapy.

"Adoptive, target-cell specific immunotherapy" refers to a form of therapy in which immune cells are transferred to tumor-bearing hosts. The immune cells have antitumor reactivity and can mediate direct or indirect antitumor effects.

"Adoptive, target-cell specific immunotherapy" or "adoptive cell therapy (ACT)" is a treatment that uses immune effector cells, such as lymphocytes with anti-tumour activity, expanded in vitro and infused into the patient with cancer. ACT using autologous tumour-infiltrating lymphocytes has emerged as the most effective treatment for patients with metastatic melanoma and can mediate objective cancer regression in approximately 50% of patients. The use of donor lymphocytes for ACT is an effective treatment for immunosuppressed patients who develop post-transplant lymphomas (reviewed in Rosenberg et al., 2008). However, the ability to genetically engineer human lymphocytes and use them to mediate cancer regression in patients, which has recently been demonstrated (see Morgan et al, 2006), has opened possibilities for the extension of ACT immunotherapy to patients with a wide variety of cancer types and is a promising new approach to cancer treatment. Thus, genetically engineering of lymphocytes with chimeric antigen receptors (CAR), such as provided by this invention, is very suitable for ACT and opens more possibilities in the treatment of cancer. Especially, since studies have clearly demonstrated that the administration of highly avid anti-tumour T cells directed against a suitable target can mediate the regression of large, vascularized, metastatic cancers in humans and provide guiding principles as well as encouragement for the further development of immunotherapy for the treatment of patients with cancer.

Methods of Treatment

Furthermore, the invention provides methods for generating antigen-specific effector cells.

The method for generating antigen-specific effector cells according to the present invention comprises
  (a) providing a multi-functional protein, nucleic acid, or expression construct according to the invention;
  (b) providing a host cell or cell line, which is selected from effector cells of the immune system, such as lymphocytes including but not limited to cytotoxic lymphocytes, T cells, cytotoxic T cells, T helper cells, Th17 T cells, natural killer (NK) cells, natural killer T (NKT) cells, mast cells, dendritic cells, killer dendritic cells, B cells;
  (c) transferring the multi-functional protein, nucleic acid, or expression construct provided in step (a) into the host cell or cell line provided in step (b);
  (d) optional, selection of the transgenic (gene-modified) cells.

The present invention also provides methods for the treatment of diseases, in particular cancer, and methods of immunotherapy, preferably including adoptive, target-cell specific immunotherapy.

The method for the treatment of diseases, in particular cancer, according to the present invention comprises
administering to a subject in a therapeutically effective amount
  (a) a multi-functional protein, a nucleic acid, an expression construct or a host cell (in particular an antigen-specific effector cell) as obtained and defined herein, and
  (b) optionally, respective excipient(s).

The method of immunotherapy, preferably including or utilizing adoptive, target-cell specific immunotherapy, according to the present invention comprises
administering to a subject in a therapeutically effective amount
  (a) a multi-functional protein, a nucleic acid, an expression construct or a host cell (in particular an antigen-specific effector cell) as obtained and defined herein, and
  (b) optionally, respective excipient(s).

A "therapeutically effective amount" of multi-functional protein, a nucleic acid, an expression construct or a host cell (in particular an antigen-specific effector cell) of this invention refers to the amount that is sufficient to treat the respective disease or achieve the respective outcome of the adoptive, target-cell specific immunotherapy.

Sequences:

SEQ ID NO:1 shows the amino acid sequence of the hinge region of human T-cell surface glycoprotein CD8 alpha chain (amino acid residues 117-178 of SEQ ID NO: 13).

SEQ ID NO:2 shows the amino acid sequence of the modified hinge region derived from the human CD8 alpha-chain hinge region.

SEQ ID NO:3 shows the amino acid sequence of human T-cell surface glycoprotein CD3 zeta chain (Swiss-Prot accession number P20963 (CD3Z_HUMAN); Isoform 3.

SEQ ID NO:4 shows the amino acid sequence of human T-cell-specific surface glycoprotein CD28 (Swiss-Prot accession number P10747 (CD28_HUMAN).

SEQ ID NO:5 shows the amino acid sequence of the fusion of the transmembrane domain and the intracellular domain of human CD28 (amino acid residues 151-220 of SEQ ID NO: 4) and the intracellular domain of human CD3 zeta chain (amino acid residues 52-163 of SEQ ID NO:3).

SEQ ID NO:6 shows the amino acid sequence of the multi-functional protein with the domains (i)[signal peptide]—(ii)[anti-ErbB2 scFv]—(iii)[modified hinge]—(iv)[transmembrane and intracellular domain of the human CD3 zeta chain].

SEQ ID NO:7 shows the amino acid sequence of the multi-functional protein with the domains (i)[signal peptide]—(ii)[anti-ErbB2 scFv]—(iii)[modified hinge]—(iv)[fusion of the transmembrane and intracellular domain of human CD28 with the intracellular domain of human CD3 zeta chain].

SEQ ID NO:8 shows the nucleotide sequence encoding for the modified hinge region in a codon-optimized form.

SEQ ID NO:9 shows the nucleotide sequence encoding for transmembrane domain and the intracellular domain of human CD3 zeta chain in a codon-optimized form.

SEQ ID NO:10 shows the nucleotide sequence encoding for the fusion of the transmembrane and intracellular domain of human CD28 with the intracellular domain of human CD3 zeta chain in a codon-optimized form.

SEQ ID NO:11 shows the nucleotide sequence encoding for the multi-functional protein with the domains (i)[signal peptide]—(ii)[anti-ErbB2 scFv]—(iii)[modified hinge]—(iv)[transmembrane and intracellular domain of the human CD3 zeta chain] in a codon-optimized form.

SEQ ID NO:12 shows the nucleotide sequence encoding for the multi-functional protein with the domains (i)[signal peptide]—(ii)[anti-ErbB2 scFv]—(iii)[modified hinge]—(iv)[fusion of the transmembrane and intracellular domain of human CD28 with the intracellular domain of human CD3 zeta chain] in a codon-optimized form.

SEQ ID NO:13 shows the amino acid sequence of human T-cell surface glycoprotein CD8 alpha chain (Swiss-Prot accession number P01732 (CD8A_HUMAN)).

The following examples and drawings illustrate the present invention without, however, limiting the same thereto.

(1A) Amino acid sequences of original (SEQ ID NO:1) and (1B) modified hinge regions (SEQ ID NO:2) derived from human CD8 alpha-chain are shown. The unpaired cysteine and the modified residue are underlined.

Figures 1A, 1B, 2:
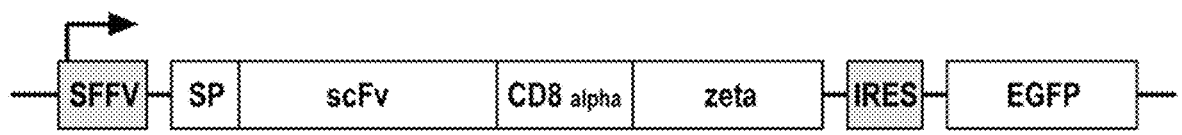
FIGS. 1A-1B Modified hinge region derived from CD8 alpha-chain.

FIG. 2 Schematic representation of the expression construct.

The sequence encoding the ErbB2-specific CAR is expressed under the control of a Spleen Focus Forming Virus promoter (SFFV) and followed by an internal ribosome entry site (IRES) and cDNA encoding enhanced green fluorescent protein (EGFP). The CAR is composed of an immunoglobulin heavy chain signal peptide (SP), an ErbB2-specific single-chain Fv antibody fragment (scFv), unmodified or modified CD8 alpha-chain hinge region as a flexible linker (CD8 alpha), and the transmembrane domain and the intracellular domain of CD3 zeta-chain as a signaling domain (zeta).

Figure 3A:
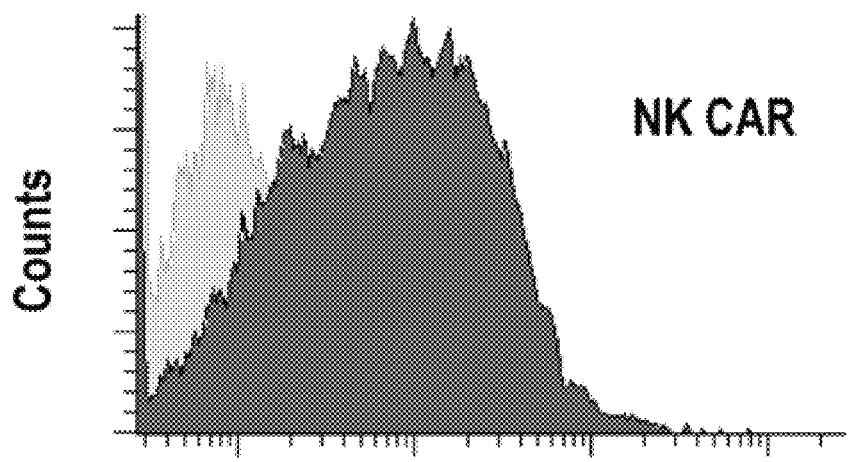
Figure 3B:
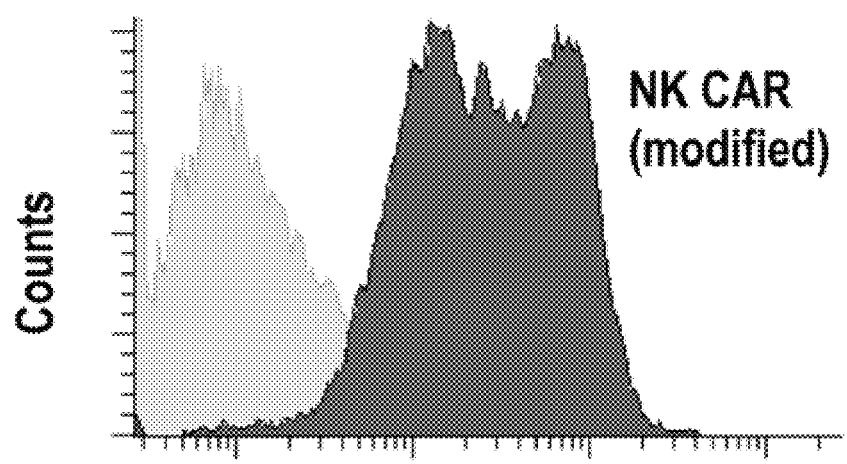

FIGS. 3A-3B Analysis of CAR surface expression in transduced NK cells.

NK cells were transduced with lentiviral vectors encoding ErbB2-specific CAR containing either unmodified (upper panel, dark gray (3A)) or modified CD8 alpha-chain hinge region (lower panel, dark gray (3B)). Gene-modified cells were selected by FACS-based sorting. Expression of CAR on the surface of NK cells was investigated by FACS analysis using ErbB2-Fc fusion protein. NK cells transduced with empty vector served as control (light gray).

Figure 4:
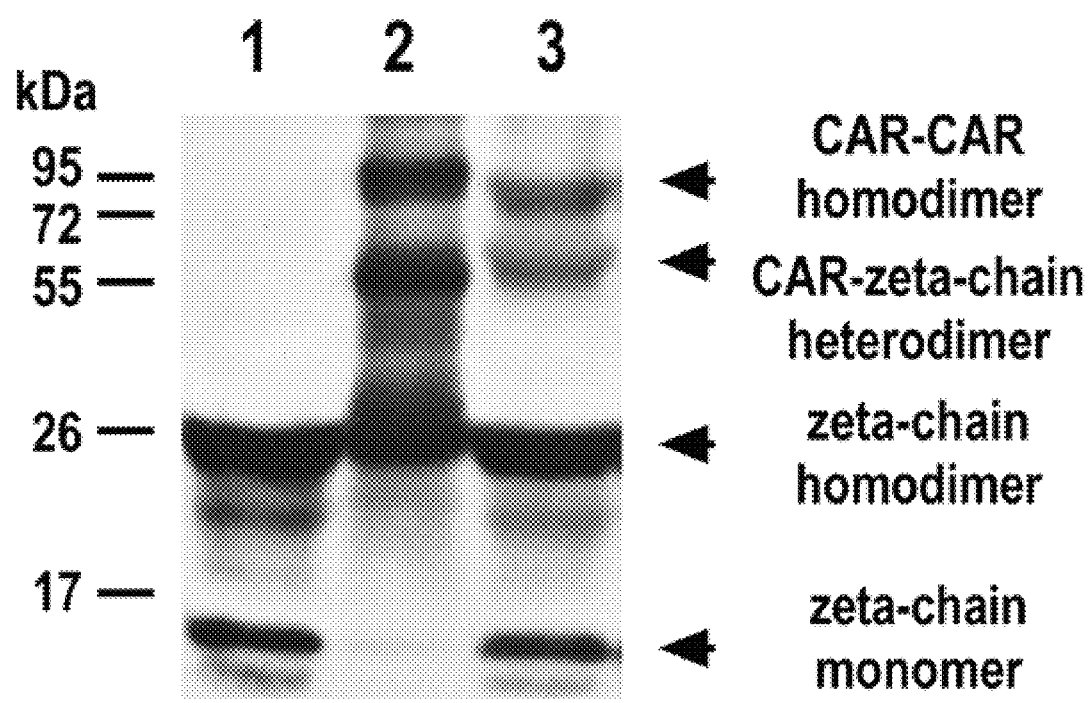

FIG. 4 Immunoblot analysis of CAR expression.

Lysates of transduced NK cells expressing ErbB2-specific CAR either containing the modified (lane 2) or unmodified CD8 alpha-chain hinge region (lane 3) were subjected to SDS-PAGE under non-reducing conditions and immunoblot analysis with anti-CD3 zeta-chain antibody as indicated. Lysate of untransduced NK cells served as control (lane 1). Monomers and homodimers of endogenous CD3 zeta-chain, CAR-CD3 zeta-chain heterodimers, and CAR homodimers are indicated.

Figure 5A:
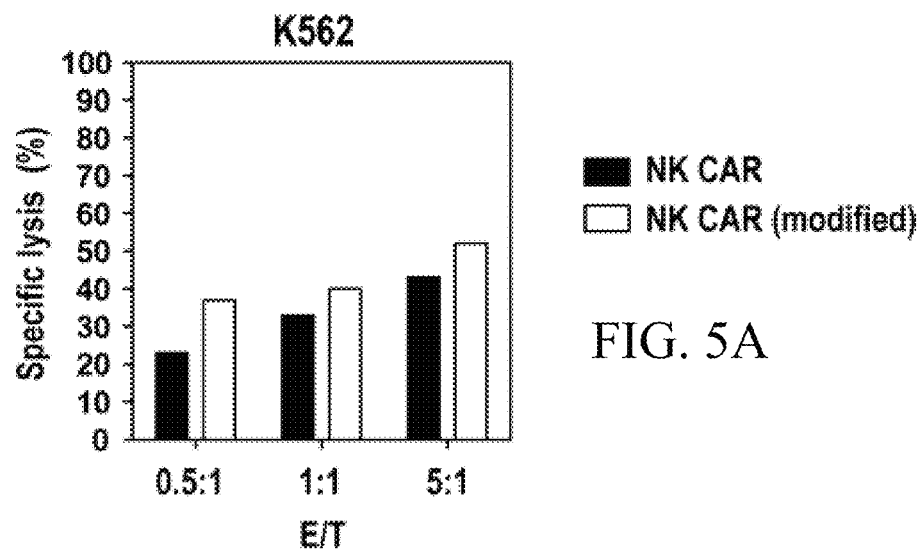
Figure 5B:
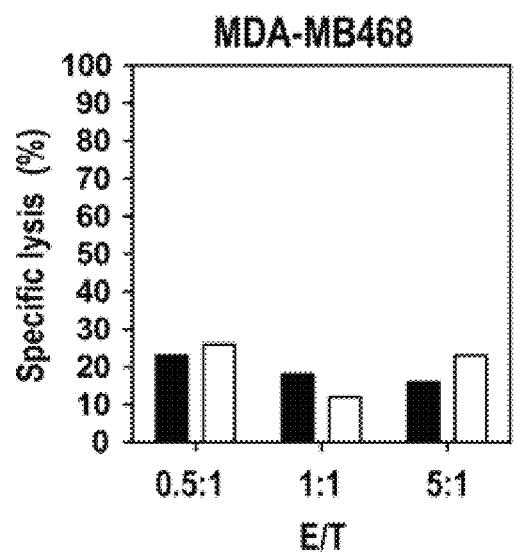
Figure 5C:
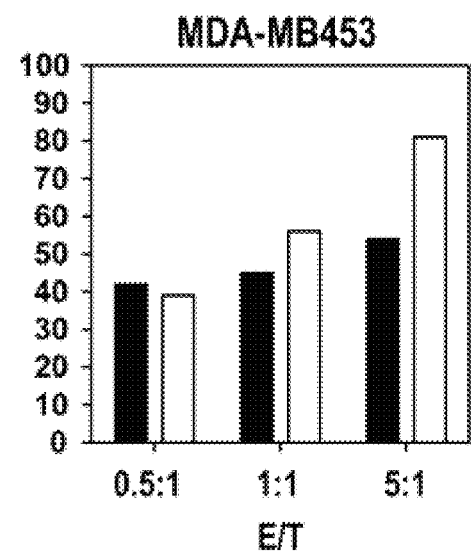

FIGS. 5A-5C Cytotoxic activity of CAR-expressing NK cells.

NK cells expressing ErbB2-specific CAR either containing the modified or unmodified CD8 alpha-chain hinge region were co-cultured at different effector to target (E:T) ratios with NK-sensitive but ErbB2-negative K562 erythroleukemic control cells (5A), ErbB2-negative MDA-MB468 breast carcinoma cells (5B), or ErbB2-positive MDA-MB453 breast carcinoma cells (5C). As shown in (5C), NK cells expressing the ErbB2-specific CAR with the modified CD8 alpha-chain hinge region showed markedly enhanced ErbB2-specific cell killing (open bars) when compared to NK cells expressing the ErbB2-specific CAR with unmodified CD8 alpha-chain hinge region (filled bars).

FIGS. 6A-6D NK cells expressing a CAR that contains CD28 and CD3 zeta chain domains.

(6A) The sequence encoding the ErbB2-specific CAR is expressed under the control of a Spleen Focus Forming Virus promoter (SFFV) and followed by an internal ribosome entry site (IRES) and cDNA encoding enhanced green fluorescent protein (EGFP). The CAR is composed of an immunoglobulin heavy chain signal peptide (SP), an ErbB2-specific single-chain Fv antibody fragment (scFv), the modified CD8 alpha-chain hinge region as a flexible linker (CD8 alpha), and CD28 and CD3 zeta-chain (zeta) as signaling domains. (6B) NK cells were transduced with the lentiviral vector shown in (6A). Gene-modified cells were selected by FACS-based sorting. Expression of CAR on the surface of NK cells was investigated by FACS analysis using ErbB2-Fc fusion protein (dark gray). Non-transduced NK cells served as control (light gray). NK cells expressing ErbB2-specific CAR containing the modified CD8 alpha-chain hinge region and CD28 and CD3 zeta-chain as signaling domains were co-cultured at different effector to target (E:T) ratios with ErbB2-negative MDA-MB468 breast carcinoma cells (6C), or ErbB2-positive MDA-MB453 breast carcinoma cells (6D). As shown in (6D), NK cells expressing the ErbB2-specific CAR with the modified CD8 alpha-chain hinge region and CD28 and CD3 zeta-chain as signaling domains showed ErbB2-specific cell killing (open bars) when compared to non-transduced NK cells included as control (filled bars).

EXAMPLES

Example 1

Construction of CAR. A cDNA fragment encoding the hinge region derived from the human CD8 alpha-chain was mutated by site-directed mutagenesis to replace the codon encoding the unpaired cysteine of the hinge region to a codon encoding a serine residue (FIGS. 1A-1B). Sequences encoding an immunoglobulin heavy chain signal peptide, a scFv antibody fragment specific for the tumor-associated surface antigen ErbB2, the modified hinge region derived from human CD8 alpha-chain, and transmembrane and intracellular domains of human CD3 zeta-chain were assembled into a single open reading frame resulting in an ErbB2-specific CAR encoding cDNA. The CAR encoding sequence was inserted into the lentiviral transfer vector SIEW for expression in lymphocytes under the control of the Spleen Focus Forming Virus promoter (FIG. 2). For comparison a lentiviral transfer vector was produced encoding a similar CAR containing the unmodified hinge region derived from the human CD8 alpha-chain.

Transduction of NK cells. VSV-G pseudotyped lentiviral vector particles were produced by transient triple transfection of 293T cells with the transfer vector together with the packaging constructs pMD-VSVG and 8.91. Lentiviral vector was used for transduction of NK cells, and transduced NK cells were enriched by two rounds of FACS sorting based on expression of enhanced green fluorescent protein (EGFP) as a marker gene encoded by the SIEW vector.

Surface expression of CAR. Expression of CAR on the surface of transduced and FACS-sorted NK cells was investigated by FACS analysis with an ErbB2-Fc fusion protein (R&D Systems) followed by APC-conjugated anti-human Fc F(ab)$_2$ fragment. NK cells transduced with CAR containing the modified CD8 alpha-chain hinge region displayed a higher overall surface expression of CAR when compared to NK cells expressing a similar CAR containing the unmodified CD8 alpha-chain hinge region (FIGS. 3A-3B).

Immunoblot analysis of CAR expression. CAR expression and multimerization in transduced and FACS-sorted NK cells was investigated by immunoblot analysis. Proteins in cell lysates of transduced cells were separated by SDS-PAGE under non-reducing conditions. Subsequent immunoblot analysis with anti-CD3 zeta-chain antibody demonstrated a marked reduction in the level of unpaired endogenous zeta-chain and higher levels of CAR-zeta-chain heterodimers and CAR homodimers in samples from NK cells expressing CAR with the modified CD8 alpha-chain hinge region when compared to NK cells expressing a similar CAR containing the unmodified CD8 alpha-chain hinge region (FIG. 4).

Cytotoxic activity of CAR-expressing NK cells. The cytotoxic activity of CAR-expressing NK cells was measured in FACS-based cytotoxicity assays. NK cells expressing ErbB2-specific CAR either containing the modified or unmodified CD8 alpha-chain hinge region displayed similar cytotoxic activity towards NK-sensitive but ErbB2-negative K562 erythroleukemic control cells, but were both unable to lyse NK-resistant and ErbB2-negative MDA-MB468 breast carcinoma cells. When cytotoxic activity towards ErbB2-positive MDA-MB453 breast carcinoma cells was tested, NK cells expressing the ErbB2-specific CAR with the modified CD8 alpha-chain hinge region showed markedly enhanced ErbB2-specific cell killing when compared to NK cells expressing the ErbB2-specific CAR with unmodified CD8 alpha-chain hinge region (FIGS. 5A-5C). These results demonstrate that the modified CAR posseses enhanced functionality.

Example 2

Figure 6A:
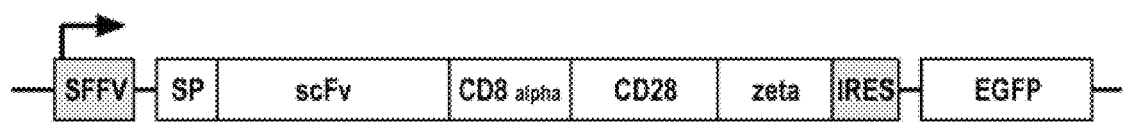

Construction of CAR containing CD28 and CD3 zeta-chain signaling domains. Sequences encoding an immunoglobulin heavy chain signal peptide, a scFv antibody fragment specific for the tumor-associated surface antigen ErbB2, the modified hinge region derived from human CD8 alpha-chain as described in Example 1, transmembrane and intracellular domains of human CD28, and the intracellular domain of human CD3 zeta-chain were assembled into a single open reading frame resulting in an ErbB2-specific CAR encoding cDNA containing CD28 and CD3 zeta-chain signaling domains. The CAR encoding sequence was inserted into the lentiviral transfer vector SIEW for expression in lymphocytes under the control of the Spleen Focus Forming Virus promoter (FIG. 6A).

Transduction of NK cells. VSV-G pseudotyped lentiviral vector particles were produced by transient triple transfection of 293T cells with the transfer vector together with the packaging constructs pMD-VSVG and 8.91. Lentiviral vector was used for transduction of NK cells, and transduced NK cells were enriched by two rounds of FACS sorting based on expression of enhanced green fluorescent protein (EGFP) as a marker gene encoded by the STEW vector.

Figure 6B:
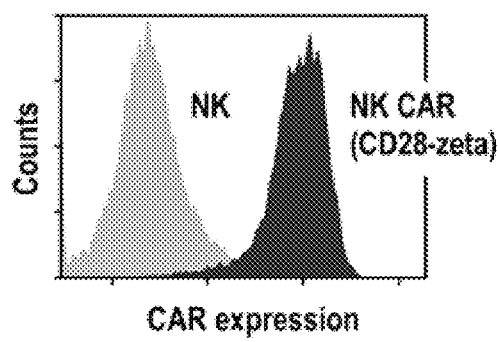

Surface expression of CAR containing CD28 and CD3 zeta-chain signaling domains. Expression of CAR containing CD28 and CD3 zeta-chain signaling domains on the surface of transduced and FACS-sorted NK cells was investigated by FACS analysis with an ErbB2-Fc fusion protein (R&D Systems) followed by APC-conjugated anti-human Fc F(ab)$_2$ fragment. NK cells transduced with CAR containing the modified CD8 alpha-chain hinge region and CD28 and CD3 zeta-chain signaling domains displayed high surface expression of CAR (FIG. 6B).

Figures 6C, 6D:
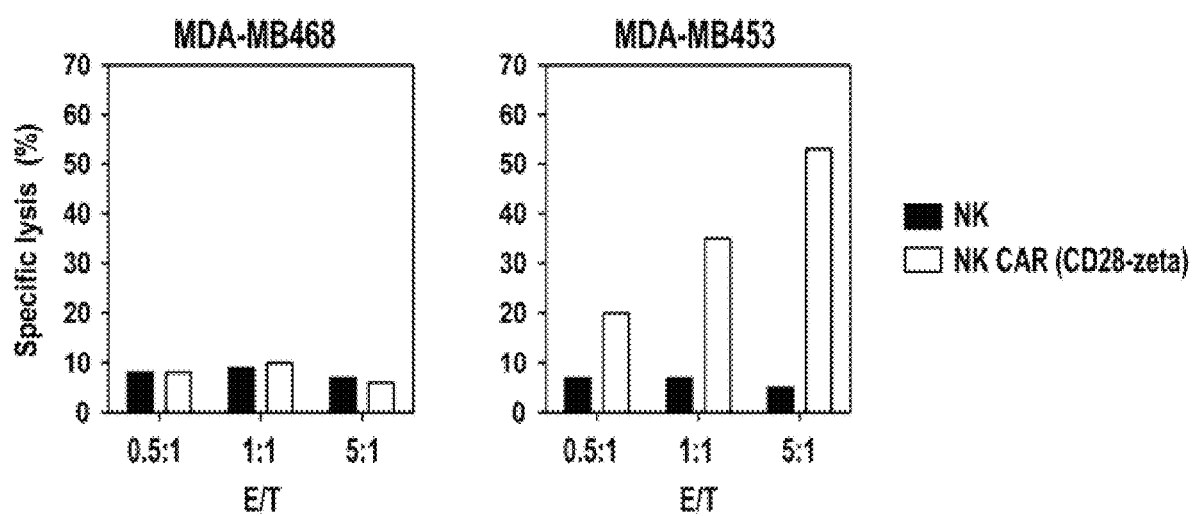

Cytotoxic activity of NK cells expressing a CAR that contains CD28 and CD3 zeta-chain signaling domains. The cytotoxic activity of NK cells expressing a CAR that contains the modified CD8 alpha-chain hinge region and CD28 and CD3 zeta-chain signaling domains was measured in FACS-based cytotoxicity assays. NK cells expressing this ErbB2-specific CAR and control NK cells not expressing a CAR were both unable to lyse NK-resistant and ErbB2-negative MDA-MB468 breast carcinoma cells (FIG. 6C). When cytotoxic activity towards ErbB2-positive MDA-MB453 breast carcinoma cells was tested, NK cells expressing the ErbB2-specific CAR with the modified CD8 alpha-chain hinge region and CD28 and CD3 zeta-chain signaling domains showed high ErbB2-specific cell killing whereas control NK cells not expressing a CAR were unable to lyse the target cells to a significant degree (FIG. 6D). These results demonstrate that the functionality of the modified CD8 alpha-chain hinge region is retained as part of a CAR that contains CD28 and CD3 zeta-chain signalling domains.

Materials and Methods (for Examples 1 and 2)

Cells and culture conditions. Human NK cells were maintained in X-VIVO10 medium supplemented with 5% human plasma and 100 IU/mL IL-2.

Production of VSV-G pseudotyped vectors in 293T cells. Vector particles were generated by transient transfection of 4×10$^6$ HEK-293T cells with a three plasmid system consisting of the packaging plasmid coding for the VSV-G envelope protein (pMD-VSVG), the glycoprotein expression plasmid encoding gag and pol (8.91), and the transfer plasmid carrying the gene of interest. Cells were transfected by calcium phosphate transfection using a total of 20 µg plasmid DNA consisting of 6.5 µg gag pol, 3.5 µg VSV-G, and 10 µg of transfer plasmids. DNA-calcium phosphate-precipitates were added dropwise to cell monolayers, and 10 mM chloroquine were added. Cell culture supernatants containing pseudotyped lentiviral vector particles were harvested 48 h later. Supernatants were sterile filtered (0.45 µm filter) and directly used for transduction of NK cells.

Lentiviral transduction. For transduction, 5×10$^5$ NK cells were seeded into a single well of a 6 well plate. Vector particles were added to the cells in the presence of 8 µg/mL polybrene and centrifuged for 60 min at 1800 rpm at 32° C. 48 h after transduction the cells were analyzed by FACS for EGFP and CAR expression.

Flow cytometric analysis. For analysis of CAR expression, transduced NK cells were incubated with 1 µg ErbB2-Fc fusion protein (R&D Systems) for 1 h at 4° C. Then cells were washed and stained with a secondary APC-coupled anti-human Fc F(ab)$_2$ antibody fragment for 20 min at 4° C. Samples were washed in FACS buffer (DPBS, 3% FCS) and resuspended in 250 µl for FACS analysis using a FACSCanto flow cytometer (BD Biosciences). Non-transduced NK cells or NK cells transduced with empty SIEW lentiviral vector served as control.

Immunoblot analysis. 5×10$^6$ NK cells were harvested and pelleted. After washing twice with DPBS, 500 µL lysis buffer (20 mM Tris, pH 7.3, 137 mM NaCl, 10% glycerol, 1% Triton X-100, 2 mM EDTA, protease inhibitors) were added to the cell pellet and incubated for 20 min on ice. Cell debris was removed by centrifugation at 14,000 rpm for 10 min at 4° C. Lämmli buffer without addition of reducing reagents was added to the cleared supernatants, and the samples were subjected to SDS-PAGE and immunoblot analysis with anti-CD3 zeta-chain antibody following standard procedures.

FACS-based cytotoxicity assays. To investigate cytotoxic activity of parental and genetically modified NK cells (effector cells, E) towards different tumor cell lines (target cells, T), a FACS-based cytotoxicity assay was used. Target cells were labeled with calcein violet AM (Molecular Probes, Invitrogen). Cells were harvested, counted and washed in calcein wash buffer (RPMI1640). The cell number was adjusted to $4\times10^6$ cells/mL, and 1.5 µL calcein violet AM dissolved in 42 µL DMSO were added to the cells. Staining of cells was performed for 30 min on ice. Then cells were washed three times with calcein wash buffer, and the cell number was adjusted to $5\times10^5$ cells/mL. To test cytotoxic activity of genetically modified NK cells, effector and labeled target cells were co-cultured at various effector to target (E/T) ratios. First, effector cells were pelleted, counted and the cell number was adjusted to $5\times10^6$ cells/mL. Appropriate dilutions were prepared. For co-culture experiments target cells were resuspended in X-VIVO medium containing 5% human plasma and 100 IU/mL of IL-2. 100 µL target cells were co-cultured with 100 µL effector cells at various E/T ratios for 2 h at 37° C. Then samples were washed once in FACS buffer. Spontaneous target-cell lysis was determined in samples only containing labeled target cells. 250 µL propidium iodide solution (1 µg/mL) were added to the samples shortly before measurement. Cells were analyzed in a FACSCanto flow cytometer (BD Biosciences). The percentage of dead target cells was determined using FACSDiVa software (BD Biosciences).

REFERENCES

Uherek C, Groner B, Wels W. Chimeric antigen receptors for the retargeting of cytotoxic effector cells. *J. Hematother. Stem Cell Res.* 10: 523-543, 2001.

Uherek C, Tonn T, Uherek B, Becker S, Schnierle B, Klingemann H G, Wels W. Retargeting of natural killer-cell cytolytic activity to ErbB2 expressing cancer cells results in efficient and selective tumor cell destruction. *Blood* 100: 1265-1273, 2002.

Fitzer-Attas C J, Schindler D G, Waks T, Eshhar Z. Harnessing Syk family tyrosine kinases as signaling domains for chimeric single chain of the variable domain receptors: optimal design for T cell activation. *J Immunol.* 160(1):145-154, 1998.

Müller T, Uherek C, Maki G, Chow K U, Schimpf A, Klingemann H G, Tonn T, Wels W S. Expression of a CD20-specific chimeric antigen receptor enhances cytotoxic activity of NK cells and overcomes NK-resistance of lymphoma and leukemia cells. *Cancer Immunol. Immunother.* 57: 411-423, 2008.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Cancer regression in patients after transfer of genetically engineered lymphocytes. *Science.* 2006 Oct. 6; 314(5796): 126-9.

Rosenberg S A, Restifo N P, Yang J C, Morgan R A, Dudley M E. Adoptive cell transfer: a clinical path to effective cancer immunotherapy. *Nat Rev Cancer.* 2008 April; 8(4): 299-308.

---

SEQUENCE LISTING

```
<160> NUMBER OF SEQ ID NOS: 13

<210> SEQ ID NO 1
<211> LENGTH: 62
<212> TYPE: PRT
<213> ORGANISM: Homo sapiens

<400> SEQUENCE: 1

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp
    50                  55                  60

<210> SEQ ID NO 2
<211> LENGTH: 62
<212> TYPE: PRT
<213> ORGANISM: Artificial sequence
<220> FEATURE:
<223> OTHER INFORMATION: Modified hinge region

<400> SEQUENCE: 2

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30
```

```
Ala Pro Thr Ile Ala Ser Gln Pro Leu Ser Leu Arg Pro Glu Ala Ser
        35                  40                  45

Arg Pro Ala Ala Gly Gly Ala Val His Thr Arg Gly Leu Asp
 50                  55                  60
```

<210> SEQ ID NO 3
<211> LENGTH: 163
<212> TYPE: PRT
<213> ORGANISM: Homo sapiens

<400> SEQUENCE: 3

```
Met Lys Trp Lys Ala Leu Phe Thr Ala Ala Ile Leu Gln Ala Gln Leu
 1               5                  10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
 50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg
```

<210> SEQ ID NO 4
<211> LENGTH: 220
<212> TYPE: PRT
<213> ORGANISM: Homo sapiens

<400> SEQUENCE: 4

```
Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125
```

```
Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 5
<211> LENGTH: 182
<212> TYPE: PRT
<213> ORGANISM: Artificial sequence
<220> FEATURE:
<223> OTHER INFORMATION: amino acid sequence of the fusion of the
      transmembrane domain and the intracellular domain of human CD28
      (amino acid residues 151-220 of SEQ ID NO. 4) and the
      intracellular domain of human CD3 zeta chain (amino acid residues
      52-163 of SEQ ID NO. 3)

<400> SEQUENCE: 5

Lys Pro Phe Trp Val Leu Val Val Val Gly Gly Val Leu Ala Cys Tyr
1               5                   10                  15

Ser Leu Leu Val Thr Val Ala Phe Ile Ile Phe Trp Val Arg Ser Lys
            20                  25                  30

Arg Ser Arg Leu Leu His Ser Asp Tyr Met Asn Met Thr Pro Arg Arg
        35                  40                  45

Pro Gly Pro Thr Arg Lys His Tyr Gln Pro Tyr Ala Pro Pro Arg Asp
    50                  55                  60

Phe Ala Ala Tyr Arg Ser Arg Val Lys Phe Ser Arg Ser Ala Asp Ala
65                  70                  75                  80

Pro Ala Tyr Gln Gln Gly Gln Asn Gln Leu Tyr Asn Glu Leu Asn Leu
                85                  90                  95

Gly Arg Arg Glu Glu Tyr Asp Val Leu Asp Lys Arg Arg Gly Arg Asp
            100                 105                 110

Pro Glu Met Gly Gly Lys Pro Arg Arg Lys Asn Pro Gln Glu Gly Leu
        115                 120                 125

Tyr Asn Glu Leu Gln Lys Asp Lys Met Ala Glu Ala Tyr Ser Glu Ile
    130                 135                 140

Gly Met Lys Gly Glu Arg Arg Arg Gly Lys Gly His Asp Gly Leu Tyr
145                 150                 155                 160

Gln Gly Leu Ser Thr Ala Thr Lys Asp Thr Tyr Asp Ala Leu His Met
                165                 170                 175

Gln Ala Leu Pro Pro Arg
            180

<210> SEQ ID NO 6
<211> LENGTH: 457
<212> TYPE: PRT
<213> ORGANISM: Artificial sequence
<220> FEATURE:
<223> OTHER INFORMATION: amino acid sequence of the multi-functional
      protein with the domains (i)[signal peptide] - (ii)[anti-ErbB2
      scFv] - (iii)[modified hinge] - (iv)[transmembrane and
      intracellular domain of the human CD3 zeta chain]
```

```
<400> SEQUENCE: 6

Met Asp Trp Ile Trp Arg Ile Leu Phe Leu Val Gly Ala Ala Thr Gly
1               5                   10                  15

Ala His Ser Gln Val Gln Leu Gln Gln Ser Gly Pro Glu Leu Lys Lys
            20                  25                  30

Pro Gly Glu Thr Val Lys Ile Ser Cys Lys Ala Ser Gly Tyr Pro Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Ser Thr Gly Glu Ser Thr Phe Ala
65                  70                  75                  80

Asp Asp Phe Lys Gly Arg Phe Asp Phe Ser Leu Glu Thr Ser Ala Asn
                85                  90                  95

Thr Ala Tyr Leu Gln Ile Asn Asn Leu Lys Ser Glu Asp Ser Ala Thr
            100                 105                 110

Tyr Phe Cys Ala Arg Trp Glu Val Tyr His Gly Tyr Val Pro Tyr Trp
        115                 120                 125

Gly Gln Gly Thr Thr Val Thr Val Ser Ser Gly Gly Gly Ser Gly
    130                 135                 140

Gly Gly Gly Ser Gly Gly Gly Ser Asp Ile Gln Leu Thr Gln Ser
145                 150                 155                 160

His Lys Phe Leu Ser Thr Ser Val Gly Asp Arg Val Ser Ile Thr Cys
                165                 170                 175

Lys Ala Ser Gln Asp Val Tyr Asn Ala Val Ala Trp Tyr Gln Gln Lys
            180                 185                 190

Pro Gly Gln Ser Pro Lys Leu Leu Ile Tyr Ser Ala Ser Ser Arg Tyr
        195                 200                 205

Thr Gly Val Pro Ser Arg Phe Thr Gly Ser Gly Ser Gly Pro Asp Phe
    210                 215                 220

Thr Phe Thr Ile Ser Ser Val Gln Ala Glu Asp Leu Ala Val Tyr Phe
225                 230                 235                 240

Cys Gln Gln His Phe Arg Thr Pro Phe Thr Phe Gly Ser Gly Thr Lys
                245                 250                 255

Leu Glu Ile Lys Ala Leu Ser Asn Ser Ile Met Tyr Phe Ser His Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Ser Arg Pro Ala Ala Gly Gly Ala Val His Thr Arg Gly
305                 310                 315                 320

Leu Asp Pro Lys Leu Cys Tyr Leu Leu Asp Gly Ile Leu Phe Ile Tyr
                325                 330                 335

Gly Val Ile Leu Thr Ala Leu Phe Leu Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415
```

```
Ser Glu Ile Gly Met Lys Gly Glu Arg Arg Arg Gly Lys Gly His Asp
                420             425                 430

Gly Leu Tyr Gln Gly Leu Ser Thr Ala Thr Lys Asp Thr Tyr Asp Ala
            435                 440                 445

Leu His Met Gln Ala Leu Pro Pro Arg
        450                 455

<210> SEQ ID NO 7
<211> LENGTH: 504
<212> TYPE: PRT
<213> ORGANISM: Artificial sequence
<220> FEATURE:
<223> OTHER INFORMATION: amino acid sequence of the multi-functional
      protein with the domains (i)[signal peptide] - (ii)[anti-ErbB2
      scFv] - (iii)[modified hinge] - (iv) [fusion of the transmembrane
      and intracellular domain of human CD28 with the intracellular
      domain

<400> SEQUENCE: 7

Met Asp Trp Ile Trp Arg Ile Leu Phe Leu Val Gly Ala Ala Thr Gly
1               5                   10                  15

Ala His Ser Gln Val Gln Leu Gln Gln Ser Gly Pro Glu Leu Lys Lys
            20                  25                  30

Pro Gly Glu Thr Val Lys Ile Ser Cys Lys Ala Ser Gly Tyr Pro Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Ser Thr Gly Glu Ser Thr Phe Ala
65                  70                  75                  80

Asp Asp Phe Lys Gly Arg Phe Asp Phe Ser Leu Glu Thr Ser Ala Asn
                85                  90                  95

Thr Ala Tyr Leu Gln Ile Asn Asn Leu Lys Ser Glu Asp Ser Ala Thr
            100                 105                 110

Tyr Phe Cys Ala Arg Trp Glu Val Tyr His Gly Tyr Val Pro Tyr Trp
        115                 120                 125

Gly Gln Gly Thr Thr Val Thr Val Ser Ser Gly Gly Gly Gly Ser Gly
    130                 135                 140

Gly Gly Gly Ser Gly Gly Gly Gly Ser Asp Ile Gln Leu Thr Gln Ser
145                 150                 155                 160

His Lys Phe Leu Ser Thr Ser Val Gly Asp Arg Val Ser Ile Thr Cys
                165                 170                 175

Lys Ala Ser Gln Asp Val Tyr Asn Ala Val Ala Trp Tyr Gln Gln Lys
            180                 185                 190

Pro Gly Gln Ser Pro Lys Leu Leu Ile Tyr Ser Ala Ser Ser Arg Tyr
        195                 200                 205

Thr Gly Val Pro Ser Arg Phe Thr Gly Ser Gly Ser Gly Pro Asp Phe
    210                 215                 220

Thr Phe Thr Ile Ser Ser Val Gln Ala Glu Asp Leu Ala Val Tyr Phe
225                 230                 235                 240

Cys Gln Gln His Phe Arg Thr Pro Phe Thr Phe Gly Ser Gly Thr Lys
                245                 250                 255

Leu Glu Ile Lys Ala Leu Ser Asn Ser Ile Met Tyr Phe Ser His Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
```

```
            290                 295                 300
Pro Glu Ala Ser Arg Pro Ala Ala Gly Gly Ala Val His Thr Arg Gly
305                 310                 315                 320

Leu Asp Lys Pro Phe Trp Val Leu Val Val Val Gly Gly Val Leu Ala
                325                 330                 335

Cys Tyr Ser Leu Leu Val Thr Val Ala Phe Ile Ile Phe Trp Val Arg
                340                 345                 350

Ser Lys Arg Ser Arg Leu Leu His Ser Asp Tyr Met Asn Met Thr Pro
                355                 360                 365

Arg Arg Pro Gly Pro Thr Arg Lys His Tyr Gln Pro Tyr Ala Pro Pro
                370                 375                 380

Arg Asp Phe Ala Ala Tyr Arg Ser Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
                420                 425                 430

Arg Asp Pro Glu Met Gly Gly Lys Pro Arg Arg Lys Asn Pro Gln Glu
                435                 440                 445

Gly Leu Tyr Asn Glu Leu Gln Lys Asp Lys Met Ala Glu Ala Tyr Ser
                450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
                500

<210> SEQ ID NO 8
<211> LENGTH: 186
<212> TYPE: DNA
<213> ORGANISM: Artificial sequence
<220> FEATURE:
<223> OTHER INFORMATION: nucleotide sequence encoding for the modified
      hinge region in a codon-optimized form

<400> SEQUENCE: 8
gccctgagca acagcatcat gtacttcagc cacttcgtgc ccgtgtttct gccccgccaag    60 cccaccacca cccctgcccc cagacccccct accccagccc ccacaatcgc cagccagccc   120
ctgagcctga ggcccgaggc cagcagacct gccgctgggg gagccgtgca caccaggggc   180
ctggac                                                              186

<210> SEQ ID NO 9
<211> LENGTH: 408
<212> TYPE: DNA
<213> ORGANISM: Artificial sequence
<220> FEATURE:
<223> OTHER INFORMATION: nucleotide sequence encoding for transmembrane
      domain and the intracellular domain of human CD3 zeta chain in a
      codon-optimized form

<400> SEQUENCE: 9
cccaagctgt gctacctgct ggacggcatc ctgttcatct acggcgtgat cctgaccgcc    60
ctgttcctga gagtgaagtt cagccgcagc gccgacgccc ctgcctacca gcagggccag   120
aaccagctgt acaacgagct gaacctgggc aggcgggagg aatacgacgt gctggacaag   180
cgcagaggcc gggaccctga gatgggcggc aagcccaggc ggaagaaccc ccaggaaggc   240
```

| | | |
|---|---|---|
| ctgtataacg aactgcagaa agacaagatg gccgaggcct acagcgagat cggcatgaag | 300 | |
| ggcgagcggc gacgcggcaa gggccacgac ggcctgtacc agggcctgtc caccgccacc | 360 | |
| aaggacacct acgacgccct gcacatgcag gccctgcctc cccgttaa | 408 | |

<210> SEQ ID NO 10
<211> LENGTH: 549
<212> TYPE: DNA
<213> ORGANISM: Artificial sequence
<220> FEATURE:
<223> OTHER INFORMATION: nucleotide sequence encoding for the fusion of
the transmembrane and intracellular domain of human CD28 with the
intracellular domain of human CD3 zeta chain in a codon-optimized
form

<400> SEQUENCE: 10

| | | |
|---|---|---|
| aagcccttct gggtgctggt cgtggtcggc ggagtgctgg cctgttacag cctgctggtc | 60 | |
| accgtggcct tcatcatctt ttgggtccgc agcaagcgga gccggctgct gcacagcgac | 120 | |
| tacatgaaca tgaccccaag gcggccaggc cccacccgga agcactacca gccctatgcc | 180 | |
| cctcctaggg acttcgccgc ctaccggtcc agagtgaagt tcagccgcag cgccgacgcc | 240 | |
| cctgcctacc agcagggcca gaaccagctg tacaacgagc tgaacctggg caggcgggag | 300 | |
| gaatacgacg tgctggacaa gcgcagaggc cgggaccctg agatgggcgg caagcccagg | 360 | |
| cggaagaacc cccaggaagg cctgtataac gaactgcaga agacaagat ggccgaggcc | 420 | |
| tacagcgaga tcggcatgaa gggcgagcgg cgacgcggca agggccacga cggcctgtac | 480 | |
| cagggcctgt ccaccgccac caaggacacc tacgacgccc tgcacatgca ggccctgcct | 540 | |
| ccccgttaa | 549 | |

<210> SEQ ID NO 11
<211> LENGTH: 1374
<212> TYPE: DNA
<213> ORGANISM: Artificial sequence
<220> FEATURE:
<223> OTHER INFORMATION: nucleotide sequence encoding for the multi-
functional protein with the domains (i)[signal peptide] - (ii)
[anti-ErbB2 scFv] - (iii)[modified hinge] - (iv)[transmembrane and
intracellular domain of the human CD3 zeta chain] in a codon-
optimized form

<400> SEQUENCE: 11

| | | |
|---|---|---|
| atggactgga tctggcggat tctgttcctg gtcggggctg ccacaggcgc ccacagccag | 60 | |
| gtgcagctgc agcagagcgg ccctgagctg aagaagcccg cgagacagt caagatcagc | 120 | |
| tgcaaggcca gcggctaccc cttcaccaac tacggcatga actgggtgaa acaggcccca | 180 | |
| ggccagggac tgaagtggat gggctggatc aacaccagca ccggcgagag cacccttcgcc | 240 | |
| gacgacttca agggcagatt cgacttcagc ctggaaacca gcgccaacac cgcctacctg | 300 | |
| cagatcaaca acctgaagag cgaggacagc gccacctact tttgcgccag atgggaggtg | 360 | |
| taccacggct acgtgcccta ctggggccag ggcaccaccc tgaccgtgtc cagcggcgga | 420 | |
| gggggctctg gcggcggagg atctggggga ggggcagcg acatccagct gacccagagc | 480 | |
| cacaagtttc tgagcaccag cgtgggcgac cgggtgtcca tcacctgcaa agccagccag | 540 | |
| gacgtgtaca acgccgtggc ctggtatcag cagaagcctg gccagagccc caagctgctg | 600 | |
| atctacagcg ccagcagccg gtacaccggc gtgccagca ggttcaccgg cagcggcagc | 660 | |
| ggcccagact tcacccttcac catcagcagc gtgcaggcca ggacctggc cgtgtacttc | 720 | |
| tgccagcagc acttccggac ccccttcacc ttcggctccg gcaccaagct ggaaatcaag | 780 | |

```
gccctgagca acagcatcat gtacttcagc cacttcgtgc ccgtgtttct gcccgccaag      840
cccaccacca cccctgcccc cagacccect accccagccc ccacaatcgc cagccagccc      900
ctgagcctga ggcccgaggc cagcagacct gccgctgggg gagccgtgca caccaggggc      960
ctggacccca agctgtgcta cctgctggac ggcatcctgt tcatctacgg cgtgatcctg     1020
accgccctgt tcctgagagt gaagttcagc cgcagcgccg acgcccctgc ctaccagcag     1080
ggccagaacc agctgtacaa cgagctgaac ctgggcaggc gggaggaata cgacgtgctg     1140
gacaagcgca gaggccggga ccctgagatg ggcggcaagc ccaggcggaa gaaccccag      1200 gaaggcctgt ataacgaact gcagaaagac aagatggccg aggcctacag cgagatcggc     1260
atgaagggcg agcggcgacg cggcaagggc cacgacggcc tgtaccaggg cctgtccacc     1320
gccaccaagg acacctacga cgccctgcac atgcaggccc tgcctccccg ttaa           1374
```

<210> SEQ ID NO 12
<211> LENGTH: 1515
<212> TYPE: DNA
<213> ORGANISM: Artificial sequence
<220> FEATURE:
<223> OTHER INFORMATION: nucleotide sequence encoding for the multi-
   functional protein with the domains (i)[signal peptide] - (ii)
   [anti-ErbB2 scFv] - (iii)[modified hinge] - (iv)[fusion of the
   transmembrane and intracellular domain of human CD28 with the
   intracellular domain

<400> SEQUENCE: 12

```
atggactgga tctggcggat tctgttcctg gtcggggctg ccacaggcgc ccacagccag       60
gtgcagctgc agcagagcgg ccctgagctg aagaagcccg gcgagacagt caagatcagc      120
tgcaaggcca gcggctaccc cttcaccaac tacggcatga actgggtgaa acaggccccca     180 ggccagggac tgaagtggat gggctggatc aacaccagcc ccggcgagag caccttcgcc      240
gacgacttca agggcagatt cgacttcagc ctggaaacca cgccaacac cgcctacctg      300 cagatcaaca acctgaagag cgaggacagc gccacctact ttgcgccag atgggaggtg      360 taccacggct acgtgcccta ctggggccag ggcaccaccg tgaccgtgtc cagcggcgga      420
gggggctctg gcggcggagg atctggggga ggggcagcg acatccagct gacccagagc      480
cacaagtttc tgagcaccag cgtgggcgac cgggtgtcca tcacctgcaa agccagccag     540
gacgtgtaca acgccgtggc ctggtatcag cagaagcctg ccagagccc caagctgctg      600 atctacagcg ccagcagccg gtacaccggc gtgcccagca ggttcaccgg cagcggcagc      660 ggccccagact tcaccttcac catcagcagc gtgcaggcc aggacctggc cgtgtacttc     720
tgccagcagc acttccggac ccccttcacc ttcggctccg gcaccaagct ggaaatcaag      780
gccctgagca acagcatcat gtacttcagc cacttcgtgc ccgtgtttct gcccgccaag     840
cccaccacca cccctgcccc cagacccct accccagccc ccacaatcgc cagccagccc      900
ctgagcctga ggcccgaggc cagcagacct gccgctgggg gagccgtgca caccaggggc      960
ctggacaagc ccttctgggt gctggtcgtg gtcggcggag tgctggcctg ttacagcctg     1020
ctggtcaccg tggccttcat catctttttgg gtccgcagca agcggagccg gctgctgcac     1080
agcgactaca tgaacatgac cccaaggcgg ccaggcccca cccggaagca ctaccagccc      1140
tatgcccctc ctagggactt cgccgcctac cggtccagag tgaagttcag ccgcagcgcc     1200
gacgcccctg cctaccagca gggccagaac cagctgtaca acgagctgaa cctgggcagg     1260
cgggaggaat acgacgtgct ggacaagcgc agaggccggg accctgagat gggcggcaag     1320
```

```
cccaggcgga agaacccca ggaaggcctg tataacgaac tgcagaaaga caagatggcc    1380
gaggcctaca gcgagatcgg catgaagggc gagcggcgac gcggcaaggg ccacgacggc    1440
ctgtaccagg gcctgtccac cgccaccaag gacacctacg acgccctgca catgcaggcc    1500
ctgcctcccc gttaa                                                     1515

<210> SEQ ID NO 13
<211> LENGTH: 235
<212> TYPE: PRT
<213> ORGANISM: Homo sapiens

<400> SEQUENCE: 13

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235
```

We claim:

1. A nucleic acid sequence comprising nucleic acids encoding:
   a linker region that does not contain a cysteine residue and is selected from the following:
   a) the amino acid sequence of SEQ ID NO. 2,
   b) an amino acid sequence having at least 95% sequence identity to SEQ ID NO. 2 under the proviso that amino acid residue 48 is a serine, and
   c) an amino acid sequence that differs in one, two or three amino acid residues from the amino acid sequence of SEQ ID NO. 2 under the proviso that amino acid residue 48 is a serine.

2. The nucleic acid sequence of claim 1, comprising: i) a nucleic acid sequence encoding the amino acid sequence of SEQ ID NO: 2 or a sequence having 95% sequence identity to SEQ ID NO: 2, or ii) a nucleic acid sequence of SEQ ID NO: 8, a sequence complementary to SEQ ID NO: 8, or a sequence having at least 95% sequence identity to SEQ ID NO: 8.

3. The nucleic acid sequence of claim 1, further comprising: i) a nucleic acid sequence encoding: a) the amino acid sequence of SEQ ID NO: 3 or 5 or a sequence having at least 95% sequence identity to the sequence of SEQ ID NO: 3 or 5 or b) the amino acid residues 29-163 of SEQ ID NO: 3; or ii) the nucleic acid sequence of SEQ ID NO: 9 or 10, a sequence having 95% sequence identity to SEQ ID NO: 9 or 10, a sequence complementary to SEQ ID NO: 9 or 10, or a sequence having at least 95% sequence identity to the sequence complementary to SEQ ID NO: 9 or 10.

4. The nucleic acid sequence of claim 1, further comprising: i) a nucleic acid sequence encoding the amino acid sequence of SEQ ID NO: 6 or 7 or a sequence having at least 95% sequence identity to the sequence of SEQ ID NO: 6 or 7, or ii) the nucleic acid sequence of SEQ ID NO: 11 or 12, a sequence having at least 95% sequence identity to the sequence of SEQ ID NO: 11 or 12, a sequence complementary to the sequence of SEQ ID NO: 11 or 12, or a sequence having at least 95% sequence identity to the sequence complementary to SEQ ID NO: 11 or 12.

5. An expression construct comprising a nucleic acid sequence of claim 1, and promoter and terminator sequences.

6. A host cell expressing a nucleic acid sequence of claim 1, wherein the host cell is an effector cell of the immune system.

7. The host cell of claim 6, wherein the effector cell of the immune system is a natural killer (NK) or a natural killer T (NKT) cell.

8. The nucleic acid sequence of claim 1, further comprising: a nucleic acid sequence encoding a target specific recognition domain and a nucleic acid sequence encoding an effector domain, wherein:

A) the nucleic acid sequence encoding the target specific recognition domain comprises:

i) a nucleic acid sequence encoding the amino acid sequence of SEQ ID NO: 6 or 7 or a sequence having at least 95% sequence identity to the sequence of SEQ ID NO: 6 or 7, or ii) the nucleic acid sequence of SEQ ID NO: 11 or 12, a sequence having at least 95% sequence identity to the sequence of SEQ ID NO: 11 or 12, a sequence complementary to the sequence of SEQ ID NO: 11 or 12, or a sequence having at least 95% sequence identity to the sequence complementary to SEQ ID NO: 11 or 12; and B) the nucleic acid sequence encoding the effector domain comprises:

i) a nucleic acid sequence encoding: a) the amino acid sequence of SEQ ID NO: 3 or 5 or a sequence having at least 95% sequence identity to the sequence of SEQ ID NO: 3 or 5 or b) the amino acid residues 29-163 of SEQ ID NO: 3; or ii) the nucleic acid sequence of SEQ ID NO: 9 or 10, a sequence having 95% sequence identity to SEQ ID NO: 9 or 10, a sequence complementary to SEQ ID NO: 9 or 10, or a sequence having at least 95% sequence identity to the sequence complementary to SEQ ID NO: 9 or 10.

* * * * *